United States Patent
Shibata et al.

(10) Patent No.: US 9,395,312 B2
(45) Date of Patent: Jul. 19, 2016

(54) METHOD FOR ASSESSING WEAR IN MOLDING MACHINE

(71) Applicant: TOYO MACHINERY & METAL CO., LTD., Akashi-shi, Hyogo (JP)

(72) Inventors: Kazuyuki Shibata, Akashi (JP); Akira Inoue, Akashi (JP); Yasutake Sawada, Akashi (JP); Kensuke Moritani, Akashi (JP)

(73) Assignee: TOYO MACHINERY & METAL CO., LTD., Akashi-shi (JP)

( * ) Notice: Subject to any disclaimer, the term of this patent is extended or adjusted under 35 U.S.C. 154(b) by 462 days.

(21) Appl. No.: 14/055,111

(22) Filed: Oct. 16, 2013

(65) Prior Publication Data

US 2014/0039808 A1    Feb. 6, 2014

Related U.S. Application Data

(63) Continuation of application No. PCT/JP2012/060719, filed on Apr. 20, 2012.

(30) Foreign Application Priority Data

Apr. 28, 2011   (JP) ................. 2011-100679

(51) Int. Cl.
   *B29C 45/76*   (2006.01)
   *B29C 45/60*   (2006.01)
   *G01N 23/00*   (2006.01)
   (Continued)

(52) U.S. Cl.
   CPC ............... *G01N 23/00* (2013.01); *B29C 45/60* (2013.01); *B29C 45/76* (2013.01);
   (Continued)

(58) Field of Classification Search
   CPC ............ B29C 45/76; B29C 45/60; B29C 3945/76173; B29C 2945/76187; G01N 3/562; G01N 3/567; G01N 3/565; G01N 3/56; G01N 2223/634; G01N 2033/00748; G01N 2033/0091; G01N 2033/0096; G01N 1/2813; G01N 1/2853; G01N 1/2866; G01N 2035/00346
   See application file for complete search history.

(56) References Cited

U.S. PATENT DOCUMENTS 5,817,928 A * 10/1998 Garvey, III ......... G01N 33/2888
                                                      324/698
5,982,847 A * 11/1999 Nelson ............... G01N 33/2858
                                                      378/45

(Continued)

FOREIGN PATENT DOCUMENTS

JP    61-272119 A    12/1986
JP    06-281436 A    10/1994

(Continued)

OTHER PUBLICATIONS

International Search Report of PCT/JP2012/060719, mailing date of Jul. 24, 2012.

*Primary Examiner* — Matthew G Marini
*Assistant Examiner* — Leo T Hinze
(74) *Attorney, Agent, or Firm* — Westerman, Hattori, Daniels & Adrian, LLP

(57) ABSTRACT

A first chromium mass concentration and a first reference mass concentration are extracted from a first test substance made by adding a predetermined amount of calcium to a predetermined amount of pellets; a reference value is calculated on the basis thereof. A second chromium mass concentration and a second reference mass concentration are extracted from a second test substance made by adding, to a predetermined amount of the substance contained in the molded part, an amount of calcium identical to the amount added to the pellets; a comparative value is calculated on the basis thereof. A screw can be determined to have wear whenever the comparative value is not less than a numerical value 60 times that of the reference value, whereas the screw can be determined not to have wear whenever the comparative value is less than a numerical value 60 times that of the reference value.

6 Claims, 3 Drawing Sheets

(51) Int. Cl.
 *G01N 33/00* (2006.01)
 *G01N 35/00* (2006.01)
 *G01N 3/56* (2006.01)

(52) U.S. Cl.
 CPC ............... *B29C 2945/76173* (2013.01); *B29C 2945/76187* (2013.01); *G01N 3/565* (2013.01); *G01N 2033/0078* (2013.01); *G01N 2033/0096* (2013.01); *G01N 2035/00346* (2013.01)

(56) References Cited

U.S. PATENT DOCUMENTS

| 7,409,775 | B2 * | 8/2008 | Kuhman | G01N 3/56 33/542 |
| 7,917,307 | B2 * | 3/2011 | Bolt | G01N 33/2888 166/250.01 |
| 8,184,290 | B2 * | 5/2012 | Hertens | G01F 1/667 356/335 |
| 2004/0011957 | A1 * | 1/2004 | Yoshiki | G01N 23/227 250/307 |

FOREIGN PATENT DOCUMENTS

| JP | 09-302455 A | 11/1997 |
| JP | 2000-280311 A | 10/2000 |
| JP | 2002-348633 A | 12/2002 |
| JP | 2003-106216 A | 4/2003 |

* cited by examiner

FIG. 3A

[Pellets]

| Element | Mass concentration [%] |
|---|---|
| 13 Al | 34.72 |
| 14 Si | 3.34 |
| 16 S | 5.66 |
| 20 Ca | 51.60 |
| 22 Ti | 4.15 |
| 24 Cr | 0.07 |
| 26 Fe | 0.43 |
| 29 Cu | 0.02 |
| 30 Zn | 0.02 |
| 42 Mo | 0.00 |

[Not worn]

| Element | Mass concentration [%] |
|---|---|
| 13 Al | 37.30 |
| 14 Si | 6.72 |
| 16 S | 5.74 |
| 20 Ca | 46.14 |
| 22 Ti | 3.33 |
| 24 Cr | 0.10 |
| 26 Fe | 0.41 |
| 29 Cu | 0.13 |
| 30 Zn | 0.12 |
| 42 Mo | 0.00 |

[Worn]

| Element | Mass concentration [%] |
|---|---|
| 13 Al | 28.71 |
| 14 Si | 3.51 |
| 16 S | 5.93 |
| 20 Ca | 43.80 |
| 22 Ti | 3.06 |
| 24 Cr | 13.91 |
| 26 Fe | 0.80 |
| 29 Cu | 0.24 |
| 30 Zn | 0.04 |
| 42 Mo | 0.00 |

A″ — 20 Ca
C″ — 24 Cr

METHOD FOR ASSESSING WEAR IN MOLDING MACHINE

CROSS REFERENCE TO RELATED APPLICATION

This application is a continuation of International application No. PCT/JP2012/060719, filed on Apr. 20, 2012, the contents of which are incorporated herein by reference.

The present application is based on and claims priority of Japanese patent application No. 2011-100679 filed on Apr. 28, 2011, the entire contents of which are hereby incorporated by reference.

BACKGROUND OF THE INVENTION

1. Field of the Invention

The present invention relates to a method for assessing wear in a molding machine for molding a molded part by injecting and filling molten resin being melted via a heating cylinder in a mold cavity of a clamped mold through forward movement of a screw, and specifically, relates to the method for assessing wear of the screw or a heating cylinder disposed slidably in the machine.

2. Description of the Related Art

In an injection molding machine for molding a molded part via injection molding, injecting and filling of molten resin to a cavity of a mold or metering of molten resin to be injected and filled to the mold cavity are performed by moving a screw disposed in a heating cylinder back and forth or rotating the same. A surface treatment is known to be provided to such screw in the injection molding machine to form a chromium (Cr) plated layer on the surface of the screw from the viewpoint of wear resistance and seize resistance (preventing galling), and with respect to such technique, Japanese Patent Application Laid-Open Publication No. H09-302455 (patent document 1) discloses a screw having an oxide layer mainly composed of iron-chromium oxide applied on a work surface of a main body of the screw for injection molding.

According to the screw disclosed in the aforementioned patent document 1, an oxide layer mainly composed of iron-chromium oxide is formed on the work surface of a screw body in order to improve the wear resistance and seize resistance thereof, but since the screw is operated in sliding motion within a heating cylinder, it is inevitable that the wear of the surface of the screw advances during use, so that in fact, the screw had to be taken out periodically from the heating cylinder for measurement of the amount of wear and assessing whether it satisfies a predetermined condition or not, so that a complex operation was required.

SUMMARY OF THE INVENTION

The present invention aims at solving the problems of the prior art, and the object thereof is to provide a method for assessing wear in a molding machine, capable of determining the wear status of a sliding member such as a heating cylinder or a screw easily without taking out the sliding member.

The present invention provides a method for assessing wear in a molding machine for molding a molded part using material containing chromium coming into contact with a sliding member, the sliding member being moved in sliding motion during operation having a chromium plating applied to a surface thereof, including: analyzing via an analyzing device components of a first test substance having a predetermined amount of a predetermined substance not contained in pellets added to a fixed amount of the pellet which is a material for molding the molded part; extracting via the analyzing device, out of the components of the first test substance being analyzed, a first chromium mass concentration C contained in the first test substance and a mass concentration of the predetermined substance contained in the first test substance as a first reference mass concentration A; calculating via a computing means a reference value X using the first chromium mass concentration C and the first reference mass concentration A based on a following Expression 1; Expression 1: $X=C/A$; analyzing via the analyzing device components of a second test substance having added a same quality and same amount of the predetermined substance added to the fixed amount of pellets to a substance taken out of the molded part having a same mass as the fixed amount of the pellets; extracting via the analyzing device, out of the components of the second test substance being analyzed, a second chromium mass concentration C' contained in the second test substance and the mass concentration of the predetermined substance contained in the second test substance as a second reference mass concentration A'; calculating via the computing means a comparative value X' using the second chromium mass concentration C' and the second reference mass concentration A' based on a following Expression 2; Expression 2: $X'=C'/A'$; and determining and assessing a wear status of the sliding member via a determining and assessing means by determining that the sliding member is worn if the comparative value X' is not less than a numerical value 60 times that of the reference value X, and determining that the sliding member is not worn and can be used if the comparative value X' is less than the numerical value 60 times that of the reference value X.

According to the present invention regarding the method for assessing wear in a molding machine, the sliding member is a screw that is operated during metering of molten material formed by melting the pellets, and/or injecting and filling the molten material formed by melting the pellets to a mold cavity.

According to the present invention regarding the method for assessing wear in a molding machine, the sliding member is a heating cylinder for melting the pellets therein.

According to the present method for assessing wear in a molding machine, the first test substance and the second test substance are respectively combusted to remove resin.

BRIEF DESCRIPTION OF THE DRAWINGS

FIG. 3A is an explanatory view showing a mass concentration corresponding to the respective elements contained in the components of a first test substance;

FIG. 3B shows an explanatory view of mass concentration corresponding to the respective elements contained in the components of a second test substance, which shows numerical values of a case where the wear of the screw falls within the range of a defined value and it is determined that the screw is not worn; and FIG. 3C shows an explanatory view of a mass concentration corresponding to the respective elements contained in the components of the second test substance, which shows numerical values of a case where the wear of the screw exceeds the defined value and it is determined that the screw is worn.

DETAILED DESCRIPTION OF THE PREFERRED EMBODIMENTS

Now, the preferred embodiments of the present invention will be described with reference to FIGS. 1 through 3C. Of course, the present invention is easily applicable to configurations other than those illustrated in the present embodiments within the scope of the present invention.

Figure 1:
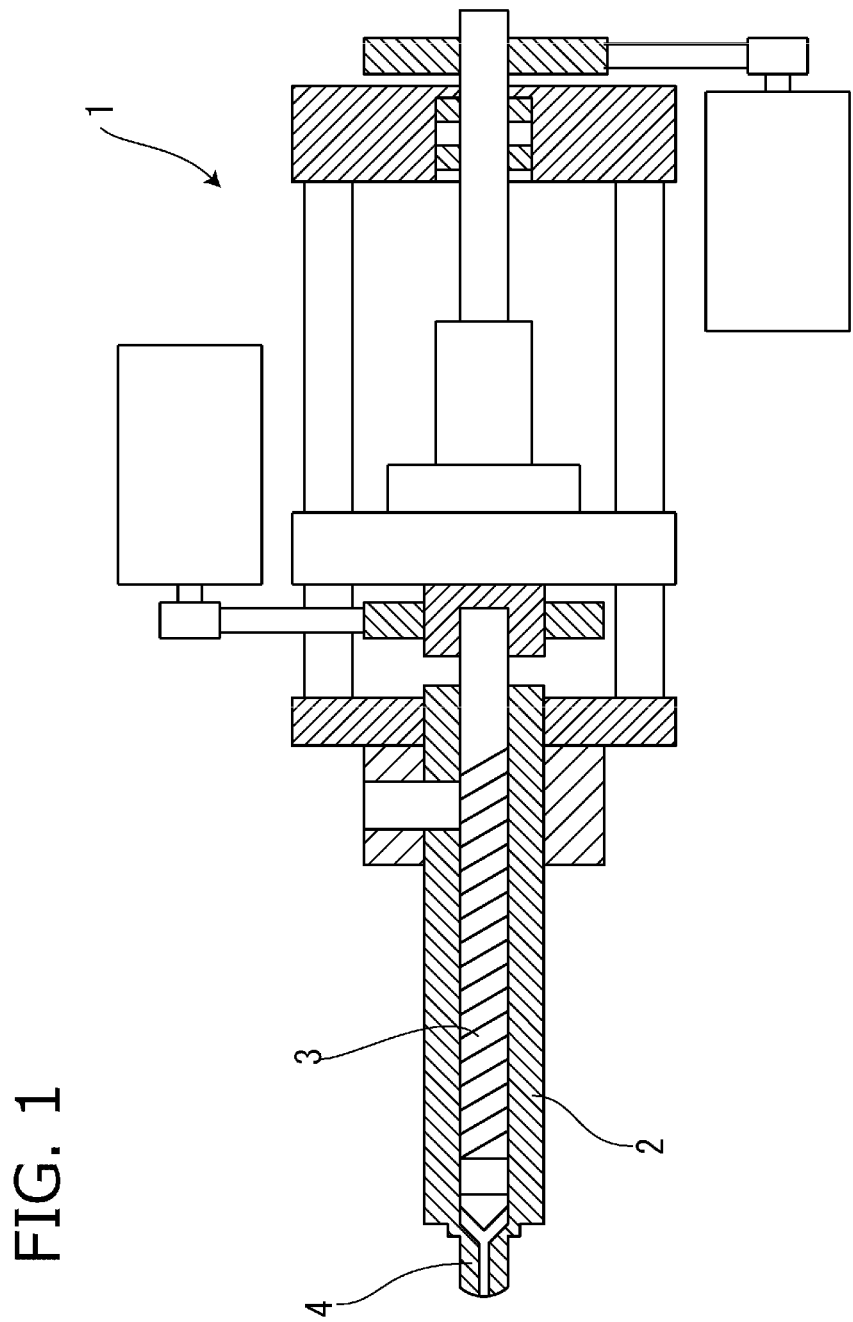
FIG. 1 is a schematic configuration diagram showing an injection unit of an injection molding machine according to one example of the present invention, wherein a portion thereof is shown in cross section.

An injection molding machine which is a molding machine according to the present embodiment includes a mold clamping unit (not shown) for opening and closing a mold and an injection unit 1, wherein as shown in FIG. 1, the injection unit 1 is composed for example of a heating cylinder 2, a screw 3 which is a sliding member disposed within the heating cylinder 2 and having a chromium-plated surface, and an injection nozzle 4, wherein the screw 3 disposed rotatably within the heating cylinder 2 is retreated during rotation to executes a metering step of molten resin (molten pellets) existing between the heating cylinder 2 and the screw 3, and then the screw 3 is moved forward during an injection step to inject molten resin through the injection nozzle 4 attached to an end of the heating cylinder 2 to fill a cavity of a mold of the mold clamping unit.

Figure 2:
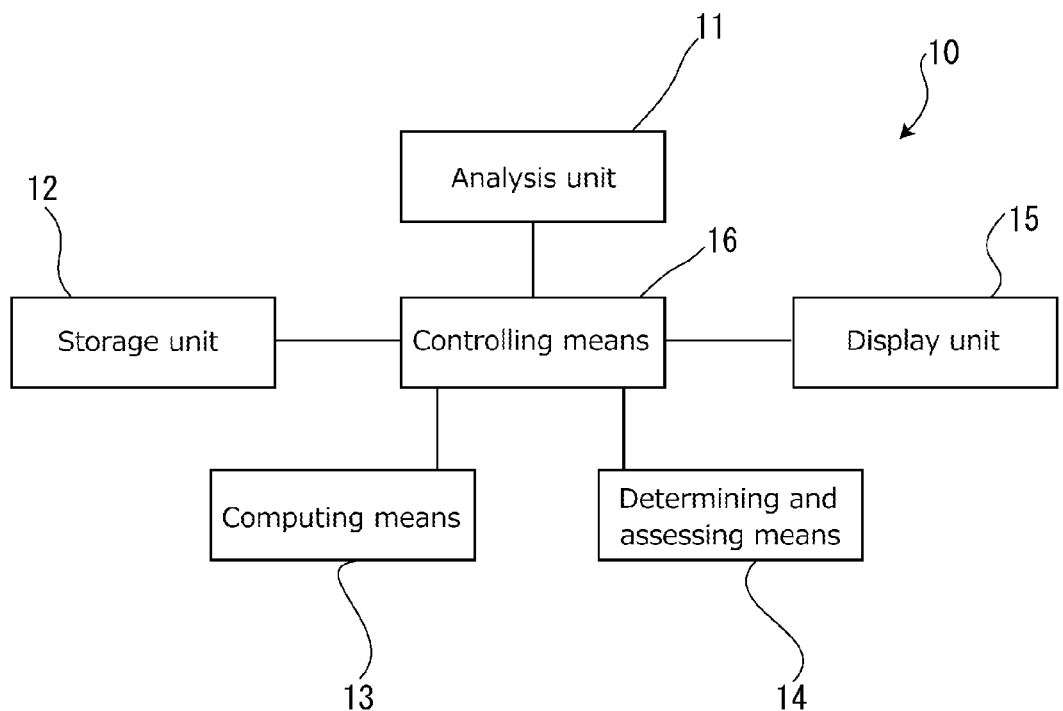
FIG. 2 is a block diagram showing a configuration of an analysis device.

FIG. 2 is a view of an analyzing device 10 capable of analyzing and assessing components of a first test substance described later contained in pellets or the like, which are materials for molding a molded part, and components of a second test substance described later included in the molded part made of synthetic resin molded by the injection molding machine. As shown in the drawing, the analyzing device 10 includes an analysis unit 11 for placing the target of analysis, a storage unit 12 storing numeric values of various components analyzed by irradiating fluorescent X-ray by the analysis unit 11, a computing means 13 for performing computing processes of the numerical values stored in the storage unit 12, a determining and assessing means 14 for comparing the respective numerical values and determining and assessing whether the values satisfy a given condition (amount of wear of the screw 3, and so on) or not based on these results, and a display unit 15 for displaying the numerical values stored in the storage unit 12 or the result of determination and assessing, wherein these operations and processes are executed based on a command output from a controlling means 16 responsible for controlling the whole injection molding machine based on the various programs stored in the storage unit 12.

Now, we will illustrate one example of a method for determining and assessing a wear status of the screw 3.

<Regarding Analysis of Components of First Test Substance>

1. First, a fixed amount (approximately 10 g) of pellets as a raw material for molding a molded part containing chromium (Cr) is placed in a crucible and heated to ignition temperature, and thereafter, heating is stopped at a time point where the resin contained in the pellets is ignited, and the target is left as it is until the fire is extinguished.

2. After the fire is extinguished, the target is heated to 600 degrees to completely remove the resin.

3. The remaining substance in the crucible is gathered and placed on an adhesive section of a double-sided tape of a predetermined size containing calcium (Ca) (that does not contain chromium). The amount being placed on the tape in this example is approximately one micro-spatula-full.

4. The sample (what was remaining in the crucible) is flattened (equalized) and smoothed on the adhesive section using the micro-spatula. At this time, the sample should not be flattened excessively so that it falls from the tape. The range in which the sample is flattened is approximately 5 mm in diameter.

5. The first test substance composed of the sample and the double-sided tape placed in the analysis unit 11 is analyzed using the fluorescent X-ray.

6. After the analysis of the first test substance is completed, the controlling means 16 stores the result of analysis of mass concentration (%) of various substances contained in the first test substance in the storage unit 12, and as shown in FIG. 3A, the result is displayed on the display unit 15 as a list.

7. Then, out of the components of the first test substance (sample+double-side tape), a first chromium mass concentration C contained in the first test substance (0.07 of FIG. 3A) and a first reference mass concentration A which is a mass concentration of the calcium of the double-sided tape contained in the first test substance (51.60 of FIG. 3A) are extracted by the controlling means 16, and the computing means 13 calculates a reference value X (0.001=0.07/51.60) based on the first chromium mass concentration C and the first reference mass concentration A using Expression 1 (X=C/A).

<Regarding Analysis of Component of Second Test Substance>

8. Next, a portion of the molded part that has been molded in the injection molding machine is cut out, and a fixed amount (approximately 10 g, equal to the fixed amount of the pellets) is taken therefrom and put into a crucible, heated to ignition temperature, and thereafter, heating is stopped at a time point where the resin contained in the pellets is ignited, and the target is left as it is until the fire is extinguished.

9. After the fire is extinguished, the target is heated to 600 degrees to completely remove the resin.

10. The remaining substance in the crucible is gathered and placed on an adhesive section of a double-sided tape of a predetermined size containing calcium (Ca) (that does not contain chromium). The amount being placed on the tape in this example is approximately one micro-spatula-full.

11. The sample (what was remaining in the crucible) is flattened (equalized) and smoothed on the adhesive section using the micro-spatula. At this time, the sample should not be flattened excessively so that it falls from the tape. The range in which the sample is flattened is approximately 5 mm in diameter.

12. The second test substance composed of the sample and the double-sided tape placed in the analysis unit 11 is analyzed using the fluorescent X-ray.

13. After the analysis of the second test substance is completed, the controlling means 16 stores the result of analysis of mass concentration (%) of various substances contained in the second test substance in the storage unit 12, and as shown in FIGS. 3B and 3C, the result is displayed on the display unit 15 as a list.

14. Thereafter, with reference to the analysis result of FIG. 3C, out of the components of the second test substance (sample+double-side tape), a second chromium mass concentration C' contained in the second test substance (13.91 of FIG. 3C) and a second reference mass concentration A' which is a mass concentration of the calcium of the double-sided tape contained in the second test substance (43.80 of FIG. 3C) are extracted by the controlling means 16, and the computing means 13 calculates a comparative value X' (0.32=13.91/43.80) based on the second chromium mass concentration C' and the second reference mass concentration A' using Expression 2 (X'=C'/A').

15. Then, when a predetermined operation is performed, the controlling means 16 executes the determining and assessing means 14, wherein if the comparative value X' (0.32) is not less than a numerical value 60 times that of the reference value X (0.001) (0.060 (0.001×60)≤0.32), it is determined that the screw 3 is worn, and the display unit 15 displays a message such as "worn" as shown in FIG. 3C. Further, for example, as based on the numerical values of FIG. 3B, if the comparative value X' (0.002=0.10/46.14) is less than a numerical value 60 times that of the reference value X (0.001) (0.002<0.060 (0.001×60)), the display unit 15 displays a message such as "not worn" as shown in FIG. 3B. As described, determination on whether or not the use of screw 3 is possible or not is performed by the analyzing device 10, and the result of the assessing is displayed visually on the display unit 15. Further, the reason for using the mass concentration of the calcium (Ca) contained in the double-sided tape is that it is recognized in advance that a fixed amount thereof is contained, and that the contained amount is relatively high.

As described, the present embodiment provides an injection molding machine for molding a molded part using material containing chromium that comes into contact with a screw 3 having a chromium plating applied to the surface of the screw 3 that slides against the heating cylinder 2 during operation, wherein the components of a first test substance having a predetermined substance (calcium contained in the double-sided tape) that it not contained in pellets added to a fixed amount of the pellets which are raw materials for forming the molded part are analyzed through irradiation of a fluorescent X-ray by the analyzing device 10, and out of the analyzed components of the first test substance, a first chromium mass concentration C contained in the first test substance and a mass concentration (a first reference mass concentration A) of the predetermined substance (calcium contained in the double-sided tape) contained in the first test substance are extracted via the controlling means 16 of the analyzing device 10, and the computing means 13 calculates the reference value X using the first chromium mass concentration C and the first reference mass concentration A via Expression 1 (X=C/A). Thereafter, the molded part already molded via the injection molding machine is cut out, for example, to take a same amount of material from the molded part as the fixed amount of the pellets, and a same amount and a same quality of the predetermined substance (calcium contained in the double-sided tape) as the substance added to the pellets is added thereto to acquire a second test substance, and the component thereof is analyzed via a fluorescent X-ray of the analyzing device, wherein out of the components of the second test substance being analyzed, a second chromium mass concentration C' contained in the second test substance and a mass concentration (a second reference mass concentration A') of the predetermined substance (calcium contained in the double-sided tape) contained in the second test substance are extracted via the controlling means 16 of the analyzing device 10, and using the second chromium mass concentration C' and the second reference mass concentration A', the computing means 13 calculates the comparative value X' via Expression 2 (X'=C'/A'), and thereafter, the determining and assessing means 14 determines and assesses the wear status of the screw 3, by determining that the screw 3 is worn if the comparative value X' is not less than a numerical value 60 times that of the reference value X, and determining that the screw 3 is not worn excessively and the screw 3 can be used if the comparative value X' is less than a numerical value 60 times that of the reference value X. Thereby, the wear status of the screw 3 that moves in sliding motion against the heating cylinder 2 can be determined based on whether the comparative value X' is not less than or less than a threshold value 60 times that of the reference value X, and the amount of wear can be assessed without having to remove the screw 3 from the injection molding machine. The present arrangement enables to solve the problem of having to perform a complex operation of taking out the screw 3, and the effect thereof is significant.

One preferred example for carrying out the present invention has been illustrated in detail, but the present invention is not restricted to the present embodiment, and various modifications are possible within the scope of the present invention. For example, the screw 3 has been described as an example of the sliding member, but the heating cylinder 2 that moves in sliding motion against the screw 3 can also be considered as the sliding member. Further according to one example of the present embodiment, the surface of the screw 3 is chromium-plated, so that X and X' are calculated using the mass concentration of chromium (C and C'), however, if the surface of the screw 3 is composed of iron (Fe), for example, iron (Fe) can be used instead of the aforementioned chromium, and this material can be selected arbitrarily based on the material of the surface of the screw 3.

The effects of the present invention are as follows.

According to the present invention, a sliding member refers to a screw that is moved in sliding motion with respect to a heating cylinder or the heating cylinder that is moved in sliding motion with respect to the screw, and the wear of such sliding member can be determined based on whether a comparative value X' is not less than a numerical value 60 times that of a reference value X. Therefore, the present invention can determine and assess the amount of wear of the screw that is moved in sliding motion with respect to the heating cylinder or the heating cylinder that is moved in sliding motion with respect to the screw without taking them out from the molding machine.

What is claimed is:

1. A method for assessing wear in a molding machine for molding a molded part using material containing chromium coming into contact with a sliding member, the sliding member being moved in sliding motion during operation and having a chromium plating applied to a surface thereof; the method comprising:

analyzing via an analyzing device components of a first test substance having a predetermined amount of a predetermined substance not contained in pellets added to a fixed amount of the pellets which are a material for molding the molded part;

out of the components of the first test substance being analyzed, extracting via the analyzing device a first chromium mass concentration C contained in the first test substance and a mass concentration of the predetermined substance contained in the first test substance as a first reference mass concentration A;

calculating via a computing means a reference value X using the first chromium mass concentration C and the first reference mass concentration A based on a following Expression 1;

$$X = C/A \qquad \text{Expression 1:}$$

analyzing via the analyzing device components of a second test substance having added a same quality and same amount of the predetermined substance added to the fixed amount of the pellets to a substance taken out of the molded part having a same mass as the fixed amount of the pellet;

out of the components of the second test substance being analyzed, extracting via the analyzing device a second chromium mass concentration C' contained in the second test substance and the mass concentration of the predetermined substance contained in the second test substance as a second reference mass concentration A';

calculating via the computing means a comparative value X' using the second chromium mass concentration C' and the second reference mass concentration A' based on a following Expression 2;

$$X' = C'/A' \qquad \text{Expression 2:}$$

and determining and assessing a wear status of the sliding member via a determining and assessing means by determining that the sliding member is worn if the comparative value X' is not less than a numerical value 60 times that of the reference value X, and determining that the sliding member is not worn and can be used if the comparative value X' is less than the numerical value 60 times that of the reference value X.

2. The method for assessing wear in a molding machine according to claim 1, wherein
the sliding member is a screw that is operated during metering of molten material formed by melting the pellets, and/or injecting and filling the molten material formed by melting the pellets to a mold cavity.

3. The method for assessing wear in a molding machine according to claim 1, wherein
the sliding member is a heating cylinder for melting the pellets therein.

4. The method for assessing wear in a molding machine according to claim 1, wherein
the first test substance and the second test substance are respectively combusted to remove resin.

5. The method for assessing wear in a molding machine according to claim 2, wherein
the first test substance and the second test substance are respectively combusted to remove resin.

6. The method for assessing wear in a molding machine according to claim 3, wherein
the first test substance and the second test substance are respectively combusted to remove resin.

* * * * *